United States Patent [19]
Miller et al.

[11] Patent Number: 5,117,829
[45] Date of Patent: Jun. 2, 1992

[54] PATIENT ALIGNMENT SYSTEM AND PROCEDURE FOR RADIATION TREATMENT

[75] Inventors: Daniel W. Miller, Yucaipa; James M. Slater, Redlands, both of Calif.

[73] Assignee: Loma Linda University Medical Center, Loma Linda, Calif.

[21] Appl. No.: 332,549

[22] Filed: Mar. 31, 1989

[51] Int. Cl.$^5$ .......................... A61B 6/00; A61B 6/03; A61N 5/10
[52] U.S. Cl. .............................. 128/653.1; 250/396 R; 250/491.1; 378/4; 378/20; 378/65; 378/145
[58] Field of Search ........................ 600/2; 128/653 R; 378/4, 20, 145, 147, 162-164, 205, 208, 901, 65, 68, 209; 250/396 R, 398, 491.1, 370.09

[56] References Cited

U.S. PATENT DOCUMENTS

| | | | |
|---|---|---|---|
| 3,783,251 | 1/1974 | Pakovich | 378/68 |
| 4,118,631 | 10/1978 | Froggatt | 378/65 |
| 4,140,129 | 2/1979 | Heinz et al. | 128/783 |
| 4,230,129 | 10/1980 | LeVeen | 378/65 |
| 4,256,966 | 3/1981 | Heinz | 378/65 |
| 4,365,341 | 12/1982 | Lam | 378/99 |
| 4,624,007 | 11/1986 | Muranushi | 378/20 |
| 4,726,046 | 2/1988 | Nunan | 378/65 |
| 4,791,934 | 12/1988 | Brunnett | 278/20 |
| 4,796,613 | 1/1989 | Heumann et al. | 128/24 A |
| 4,819,257 | 4/1989 | Grasser et al. | 378/62 |
| 4,891,829 | 1/1990 | Deckman et al. | 378/19 |
| 4,905,267 | 2/1990 | Miller et al. | 378/68 |
| 4,907,251 | 3/1990 | Mork et al. | 378/39 |

Primary Examiner—Lee S. Cohen
Assistant Examiner—K. M. Pfaffle
Attorney, Agent, or Firm—Robert R. Meads

[57] ABSTRACT

Accurate and repeatable patient alignment with a charged-particle beam of a radiation beam therapy system, such as a proton beam delivery system, is provided. The patient is immobilized within a form-fit patient pod. Reference radiographs are prepared that are used for repositioning the patient within the pod on subsequent occasions. CT scan data of a particular tissue volume of interest, such as a region of the patient wherein a cancerous tumor is located, is obtained while the patient remains in the pod. The CT scan data is used to prepare a treatment plan for the patient. The treatment plan includes identifying an isocenter within the tissue volume at which the beam is to be directed from a selected angle(s). A computer simulation of the treatment plan may be performed to optimize the treatment plan, i.e., to help identify the number of beams and treatment angles that will best irradiate the cancerous cells. Once the treatment plan is finalized, the patient is repositioned within the pod and a physical simulation of the treatment plan is carried out to verify that the selected cancerous cells will be properly irradiated. Finally, the treatment plan is carried out by irradiating the cancerous cells with the charged-particle beam in accordance with the treatment plan.

17 Claims, 11 Drawing Sheets

PATIENT ALIGNMENT SYSTEM AND PROCEDURE FOR RADIATION TREATMENT

BACKGROUND

The present invention relates to radiation beam therapy systems and more particularly to an improved system and procedure for repeatedly aligning a tumor or other desired tissue area in a patient with a radiation beam of the radiation beam therapy system. Such a system and procedure allows the desired tissue area, e.g., the tumor, to be positioned accurately relative to the radiation beam for any number of successive radiation treatments.

Radiation has been used for many years in an attempt to control cancer by killing cancerous cells. However, in order to be effective, the radiation absorbed by the selected cancerous cells (the "tumor") must be sufficient to kill the cancerous cells, while the radiation absorbed by surrounding non-cancerous cells must be kept at levels low enough to prevent permanent damage to the non-cancerous cells. As a consequence, a less than optimal total dose of radiation must frequently be used to reduce unacceptable normal tissue damage. What is clearly needed, therefore, is an approach for better controlling the radiation dose delivered to the body tissue, and more specifically for increasing the radiation dose delivered to the tumor, while reducing the radiation dose delivered to surrounding normal tissue.

It is known that heavy charged particles, such as protons, offer significant advantages over other forms of radiation, such as electrons, gamma rays, or X-rays, in controlling the radiation dose delivered to the body tissue. This is because protons of a specific energy have a definite range or penetration depth in matter. They lose energy by collisions with atoms, and finally stop, all within a few millimeters of a known depth. More significantly, they deposit most of their energy within a small distance of the end of this penetration depth, termed the Bragg peak after its discoverer. This penetration depth depends only on the energy of the protons. Hence, by carefully controlling the energy of a proton beam, and by directing the beam to a known tumor location, a good kill rate of cancerous cells can be achieved while largely sparing nearby healthy tissue.

To this end, radiation beam therapy systems, including proton beam delivery systems, are known in the art. See, e.g., Chu, W. "NCI Program Project Proposal," Lawrence Berkeley Laboratory, Oct. 14, 1987; Renner et al., "Wobbler Facility for Biomedical Experiments," Med. Phys., Vol. 14, No. 5, pp 825-34 (September/October 1987). However, such systems are generally cumbersome and/or inefficient to operate, or are limited in their ability to accurately direct the charged particle beam to all possible tumor locations. An improved proton beam delivery system has thus been proposed and is currently being built for installation at the Loma Linda University Medical Center in Loma Linda, Calif. Features of the Loma Linda system of interest to the present invention are described more fully in the following U.S. Patent Applications:

1. Ser. No. 07/163,611, filed Mar. 3, 1988, entitled "Multi-Station Proton Beam Therapy System" now U.S. Pat. No. 4,870,287,
2. Ser. No. 07/178,471, filed Apr. 17, 1988, entitled "Roller-Supported, Modular, Isocentric Gantry and Method of Assembly" now U.S. Pat. No. 4,917,344, issued Apr. 17, 1990.
3. Ser. No. 07/187,722, filed Apr. 29, 1988, entitled "Method of Assembly and Whole Body, Patient Positioning and Repositioning Support For Use In Radiation Beam Therapy Systems" now U.S. Pat. No. 4,905,267 issued Feb. 27, 1990,
4. Ser. No. 07/332,254, filed Mar. 31, 1989, entitled "Raster Scan Control System For A Charged Particle Beam."

All of the above-identified patent applications are assigned to Loma Linda University Medical Center, as is the instant application. Further, all of these applications are incorporated herein by reference.

Despite the advantages of proton therapy, however, such advantages are of little consequence if the proton beam cannot be accurately and repeatedly directed to the desired tumor location. The beam must be accurately directed to the tumor location in order to prevent damage to surrounding tissue. The beam must be repeatedly directed to the tumor location because exposure of the cancerous cells to the proton beam is generally administered though a series of exposure treatments, typically given several days or weeks apart from each other.

Unfortunately, unlike X-rays and some other forms of radiation, the proton beam does not create an image that can be used to help in the alignment process. Hence, in order to accurately direct the beam to a selected tissue location, other image-creating techniques must be used to provide the requisite alignment information. Further, in order to assure that the requisite alignment can be achieved over and over again, such image-creating techniques must utilize a repeatable reference image, or equivalent reference data, that provides the necessary baseline reference informatioin for future alignments. The present invention is directed to a system and procedure that accomplishes these goals.

SUMMARY OF THE INVENTION

The present invention provides a system and method for aligning a patient for proton or other charged-particle treatment. Specifically, the present invention provides a system and method for accurately and repeatedly aligning a specified tissue volume of the patient, such as a cluster or group of cancerous cells, with the charged-particle beam of a radiation therapy system.

In accordance with the method of the invention, the patient is first immobilized within a form-fit patient pod. Reference radiographs are then prepared that may be used for repositioning the patient within the pod on subsequent occasions. Further, while the patient is still in the pod, CT scan data of the particular tissue volume of interest, i.e., that region of the patient where the cancerous tumor is located, is obtained. After the reference radiographs and CT scan data are obtained, the patient is allowed to return home. The CT scan data is analyzed and used to prepare a treatment plan for the patient. The treatment plane includes identifying an isocenter within the tissue volume at which the proton beam is to be directed from selected angles, and preparing digitally reconstructed radiographs (DRR's) from the CT data for each beam angle. A computer simulation of the treatment plan may optionally be performed to help identify the optimum number of beams and treatment angles that will best irradiate the cancerous cells. Once the treatment plan is finalized, the patient is brought back to the treatment location and carefully repositioned within the pod. A physical simulation of the treatment plan is then carried out to verify that the selected cancerous cells will be properly irradiated by the treatment plan. If the physical simulation verifies that the treatment plan will properly irradiate the cancerous cells without significantly irradiating non-cancerous cells, the treatment plan is executed by irradiating the cancerous cells with the proton beam in accordance with the plan.

The system provided by the invention includes, in addition to the beam delivery system that ultimately administers the radiation beam to the patient in accordance with the specified treatment plan, a form-fitting pod in which the patient is placed in order to immobilize the patient, and a simulation system for simulating the delivery of the radiation dose to the patient. This simulation system advantageously provides a safe and efficient mechanism for formulating and optimizing a particular treatment plan suited for the particular patient. Further, once the treatment plan has been formulated and optimized, whcih optimizing may optionally include computer simulation of the proposed treatment, the simulation system allows the treatment plan to be verified through physical simulation involving the patient. This physical simulation advantageously assures that the radiation beam is delivered to the patient only when the radiation beam is properly aligned with the tumor.

The simulation system includes a computer, or equivalent processor, coupled to a conventional X-ray system (or equivalent exposure system). The X-ray system provides reference radiographs or image information of the tissue volume that is to be treated. This information is used to assure that the patient is always positioned correctly within the pod. The pod, in turn, is mechanically attached to a table, couch or other support of the X-ray system, which table, couch or support is selectively positioned relative to the exposing x-ray beam so as to expose a desired tissue volume of the patient. A conventional CT scan system is further utilized to help initialize the simulation system by providing a sequence of slices, or cross-sectional images, of the treatment area. These CT slices, when combined, provide three-dimensional data of the tissue volume within the patient that is to be treated. Such data advantageously provides the basis for formulating a treatment plan. In particular, an isocenter location is selected and marked that identifies the particular location within the treatment volume at which the treatment beam should be directed. Depending upon the shape, size and location of the target tissue within the treatment volume, several treatment beams may be selected for irradiating the target tissue at selected angles and intensity levels. A computer simulation of the irradiation of the treatment volume by such beams may further be carried out in order to optimize the treatment plan.

For each beam selected as part of the treatment plan, at least one digitally reconstructed radiograph (DRR) is genrated from the CT scan data depicting the radiograph that would result when looking at the treatment volume from the same angle as the beam. Further, the treatment plan computes the settings needed by the simulator system and the radiation therapy system, e.g., to adjust the position of the table, couch, or other support, to direct the beam (whether a simulated beam or an actual beam) to the isocenter location.

The physical simulation is carried out by repositioning the patient within the pod and positioning the pod within the X-ray system so that the X-rays enter the tissue volume at the same angle as specified for a particle radiation beam in accordance with the treatment plan. The resulting physical simulation radiograph (PSR) is compared to the appropriate DRR to verify that it is essentially the same. If the comparison is essentially the same, then the patient and pod are moved to the beam delivery system and the pod is positioned so that the radiation beam will enter the tissue volume at the desired angle. However, before actually irradiating the target tissue with the radiation beam, a further X-ray exposure of the tissue volume is made using an X-ray source mounted in the nozzle of the beam delivery system. This X-ray source is mounted to provide X-ray radiation to the tissue volume that is substantially aligned with the radiation dose delivered by the radiation beam. The X-ray radiation from the nozzle of the beam delivery system produces yet another radiograph which is compared with the appropriate DRR and/or the PSR to verify that the correct entry angle for the beam and correct patient position have been achieved.

Advantageously, the comparison between a given radiograph and its corresponding DRR may be carried out digitally using the computer or equivalent processing device.

The present invention may thus be characterized, in accordance with one aspect thereof, as a method for irradiating a volume of tissue within a patient, e.g., a tumor, with a charged-particle beam. The irradiation method includes the steps of: (a) immobilizing the patient; (b) obtaining CT scan data of a region of tissue within the immobilized patient that includes the volume of tissue to be irradiated; (c) preparing a treatment plan using the CT scan data, the treatment plan identifying an isocenter point having a fixed geometrical relationship relative to the volume of tissue (tumor) at which the charged-particle beam is to be directed, the treatment plan further generating an image reconstructed from the CT scan data that identifies the manner in which the volume of tissue (tumor) should appear when viewed through the isocenter point; (d) verifying the treatment plane by: (1) directing an image-forming beam at the isocenter poiint, the image-forming beam producing an image of the tissue through which it passes, and (2) comparing the image formed by the image-forming beam with the reconstructed image from the CT scan data; and (e) executing the treatment plan by directing the charged-particle beam at the isocenter point.

In accordance with another aspect of the invention, the invention may be characterized as a method for aligning a charged-particles beam with a volume of tissue of a patient undergoing radiation therapy. This alignment method comprises the steps of: (1) immobilizing the patient; (2) digitally mapping the tissue densities of the patient in the region surrounding the volume of tissue; (3) identifying and marking that data included within the data defined in step (2) that defines the volume of tissue that is to be irradiated by the charged-particle beam; (4) reconstructing at least one image of the tissue densities from the digitally mapped tissue densities, this at least one reconstructed image having a view line normal thereto that passes through the data marked in step (3); (5) forming a radiographic image of the patient's tissue taken along the view line; (6) quantitatively comparing the radiographic image to the reconstructed image; (7) adjusting the position of the immobilized patient relative to the radiographic image until the differences, if any, between the radiographic image and the reconstructed image are minimized; and (8) aligning the charged-particle beam to be delivered to the volume of tissue with the view line of the radiographic image once the diffences between the radiographic and reconstructed images have been minimized.

Further, in accordance with still another aspect of the invention, the invention may be characterized as a system used for aligning a charged-particle beam with a volume of tissue in a patient undergoing radiation therapy. Such a system includes: means for immobilizing the patient; means for digitally mapping the tissue densities of the patient in the region surrounding the volume of tissue, the digitally mapping means providing digitally mapped tissue density data that defines the tissue surrounding and including the volume of tissue; means for identifying and marking that data within the digitally mapped tissue density data that digitally defines the volume of tissue that is to be irradiated by the charged-particle beam; means for reconstructing a least one image of the tissue densities from the digitally mapped tissue density data, the at least one reconstructed image having a view line normal thereto that passes through the marked data; means for forming a radiographic image of the tissue of the patient taken along the view line; means for quantitatively comparing the radiographic image to the reconstructed image; means for adjusting the position of the immobilized patient relative to the radiographic image until the differences, if any, between the radiographic image and the reconstructed image are minimized; and means for aligning the charged-particle beam to be delivered to the volume of tissue with the view line of the radiographic image after the differences between the radiographic and reconstructed images have been minimized.

It is a feature of the present invention to provide a patient alignment system that accurately aligns a selected tissue volume of a patient with the radiation beam of a radiation therapy system.

It is a further feature of the invention to provide such an alignment system wherein the requisite alignment can be repeated over and over again as the patient returns to the radiation therapy facility to receive subsequent radiation therapy.

It is still another feature of the invention to provide a patient alignment system that is especially suited for aligning a proton beam with a selected tissue volume of the patient that is to be irradiated with the proton beam, the proton beam itself not providing any image information that can be used to help in the aligning process.

It is yet another feature of the invention to provide a patient alignment system and procedure that can be carried out with minimal discomfort and inconvenience to the patient.

It is still a further feature of the invention to provide such a patient alignment system that includes a procedure for optimally preparing a treatment plan that when executed efficiency attacks or kills only the cancerous cells and does not significantly affect surrounding non-cancerous cells.

Yet another feature of the invention is to provide such a patient alignment system wherein the treatment plan can be optimized through computer simulation.

Still another feature of the invention is to provide such a patient alignment system wherein the optimized treatment plan can be physically verified prior to its execution.

BRIEF DESCRIPTION OF THE DRAWINGS

The above and other advantages and features of the present invention will be more apparent from the following more particular description thereof, presented in conjunction with the following drawings, wherein.

DETAILED DESCRIPTION

The following description is of the best presently contemplated mode of practicing the invention. This description is not to be taken in a limiting sense but is made merely for the purpose of describing the general principles of the invention. The scope of the invention should be ascertained with reference to the claims.

In the description that follows, it is noted that like numerals are used to describe like parts or elements throughout all of the figures.

Figure 1:
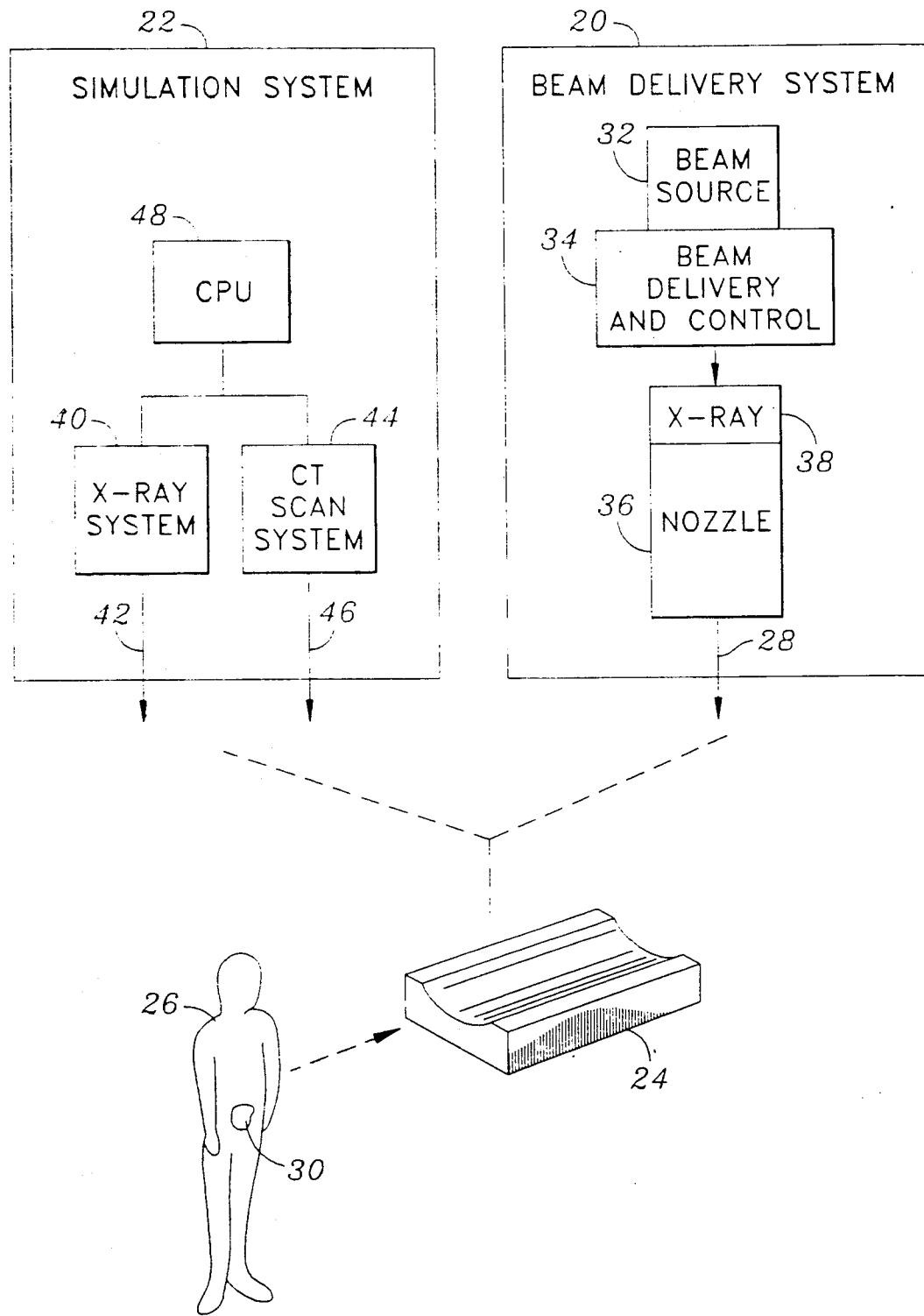
FIG. 1 is a block diagram illustrating the main components used by the alignment system of the present invention.

Referring first to FIG. 1, the main components that are used with the alignment system of the present invention are illustrated in block diagram form. Basically, these elements include a beam delivery system 20, a simulation system 22, a patient pod 24, and a patient 26. It is the function of the beam delivery system 20 to provide a charged-particle beam 28, such as a proton beam, that can be used to selectively irradiate a tumor or other target tissue volume 30 within the patient 26. This beam 28 is provided from a beam source 32, directed through a beam delivery and control system 34, and eventually guided through a nozzle structure 36 to the patient 26 and pod 24. Included in the nozzle structure 36 is a source of X-rays 38. X-rays from this source 38 are used immediately prior to delivery of the beam 28 in order to verify that a proper alignment with the target tissue volume 30 has been achieved.

It is the function of the simulation system 22 to provide X-ray (or equivalent) radiographs of the patient 26 when positioned within the pod 24. To this end an X-ray system 40 is included within the simulation system 22 for selectively producing a beam of X-rays 42. Radiographs produced from the X-rays 42 are used to properly align the patient within the pod 24, or to physically simulate the application of the beam 28 to the patient. Advantageously, as explained below, such physical simulation allows the alignment of the beam 28 to be verified prior to the actual delivery of the beam 28 to the patient.

It is a further function of the simulation system to generate Computed Tomography (CT) image data (frequently referred to as CAT scan data) of the tissue volume surrounding the target tissue 30. To this end, the simulation system includes a conventional CT scan system 44 that scans the target tissue volume 30 with a scanning beam 46 in order to generate image data that accurately defines the volume 30. This image data is used to help formulate a treatment plan, as well as to generate digitally reconstructed radiographs (DRR's) for any selected viewing angle of the target tissue 30. Such DRR's are used in the physical simulation mentioned above, and as explained more fully below.

A computer, or central processing unit (CPU) 48 also forms part of the simulation system 22. This CPU 48 is programmed in conventional manner in order to appropriately control the X-ray system 40 and the CT scan System 44, as well as to store, retrieve, and generate desired image data, such as the DRR's referenced above. Further, the CPU 48 carries out the physical simulation performed by the simulation system 22, performs comparisons between reference or other radiographs and DRR's, and performs computer simulations of a selected treatment plan, thereby aiding in the formulation and optimization of such treatment plans. Of course, rather than a single computer or CPU, the simulator system 22 may include separately programmed computers for the X-ray and CT scan systems and for generating the DRR's.

It is the function of the patient pod 24 to immobilize the patient 26 during the simulation and treatment procedures. This pod 24 is customized to form-fit a particular patient. Further details related to the pod 24 may be found in the above-referenced patent application entitled "Method of Assembly and Whole Body, Patient Positioning and Repositioning Support For Use in Radiation Beam Therapy Systems".

Figure 2:
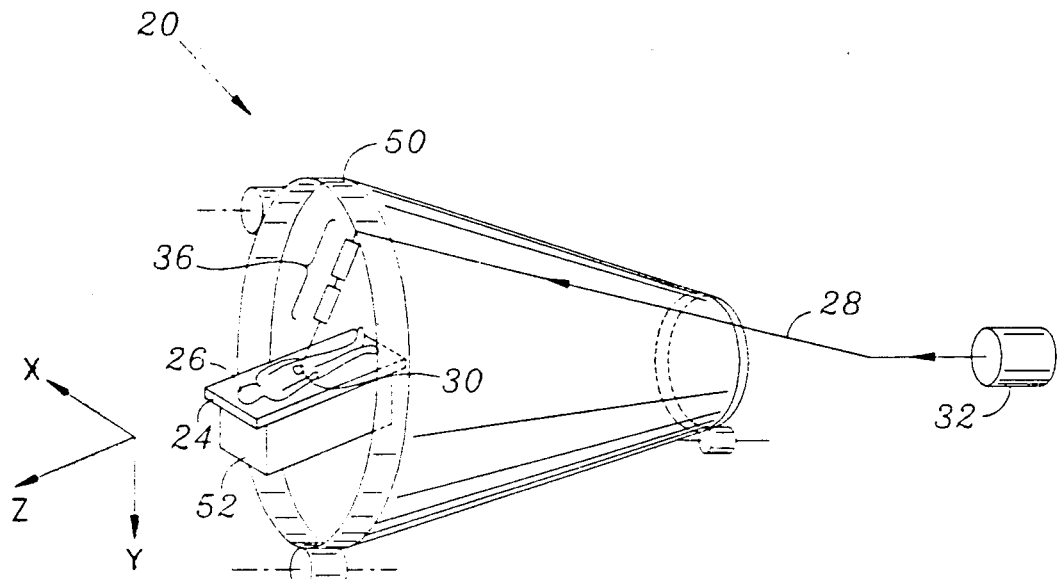
FIG. 2 is a simplified schematic representation of the beam delivery system of FIG. 1 and illustrates how such a system is used to irradiate a desired target volume within a patient.

Referring next to FIG. 2, a simplified schematic representation of the primary mechanical elements of the beam delivery system 20 is shown. The beam source 32 provides an accelerated charged-particle beam 28, such as a proton beam, having a prescribed energy. The beam 28 is directed through a rotatable gantry 50 where it is directed, using conventional means, through the nozzle 36. This nozzle 36 includes fast and slow scan magnets, as well as appropriate collimator devices that confine the beam 28 to the target volume 30 within the patient 26. The nozzle also includes an appropriate X-ray source 38 (FIG. 1). The patient is held in the patient pod 26, which pod is supported by a table 52. The table 52 (and hence the pod 24 and patient 26), as well as the gantry 50, may each be selectively rotated and translated relative to each other in order to allow the beam 28 to strike the target volume 30 from any desired angle and direction. For this purpose an XYZ coordinate system is defined, as shown in FIG. 2, wherein the Z axis is the patient's head-to-toe direction, the Y axis is into the patient, and the X axis is across the width of the patient. It is to be understood that this coordinate system is for reference purposes only, and that other reference systems and coordinate systems could just as easily be employed. Conventional means, not shown, are used to effectuate the rotating of the gantry 50 and the positioning of the table 52.

Figure 3:
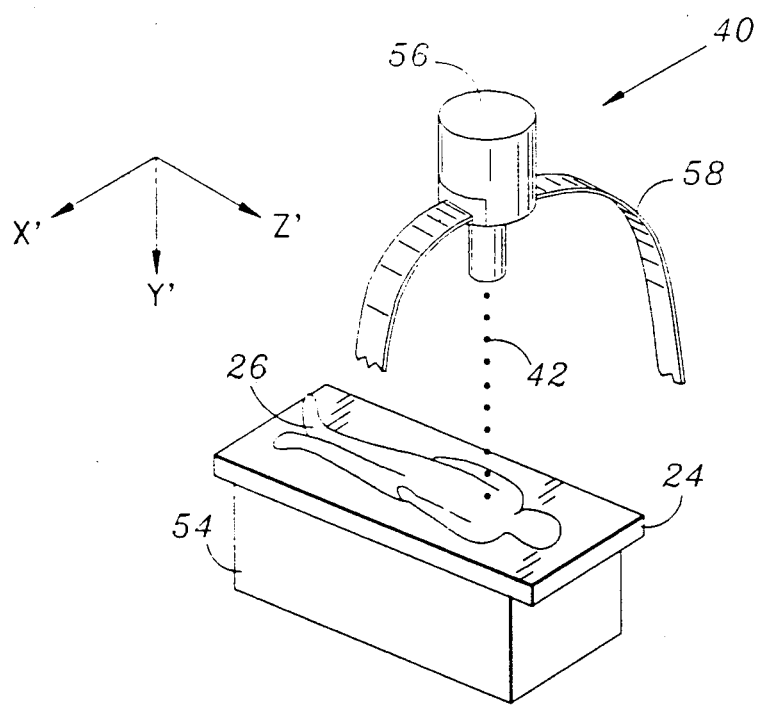
FIG. 3 is a simplified schematic representation of the X-ray system used as part of the simulation system of the present invention.

Referring next to FIG. 3, a simplified schematic representation of some of the components of the X-ray system 40 of the simulation system 22 (FIG. 1) is illustrated. Additional elements of the X-ray system are described below in connection with the description of the block diagram of FIG. 9. The X-ray system 40 includes an X-ray source 56 that is mounted for movement on a suitable rotatable structure 58. Conventional means, not shown, are used to effectuate the rotating or other movement of the X-ray source 56 and the positioning of the table 54. The patient 26 and pod 24 are supported on a table or couch 54. As with the gantry and table of the beam delivery system 20 (FIG. 2), both the X-ray source 56 and the table or couch 54 (and hence the pod 24 and patient 26), may each be selectively rotated or otherwise positioned relative to each other in order to allow the X-ray beams 42 to strike the target volume 30 from any desired angle and direction. For this purpose an X'Y'Z' coordinate system is defined, as shown in FIG. 3, wherein the Z' axis is the patient's head-to-toe direction, the Y' axis is into the patients, and the X' axis is across the width of the patient. The "prime" designator used with the X, Y, or Z coordinates is used to distinguish this "simulator" coordinate system from the beam delivery coordinate system shown in FIG. 2. These coordinate systems need not be the same, although they could be the same, if desired.

Figure 4:
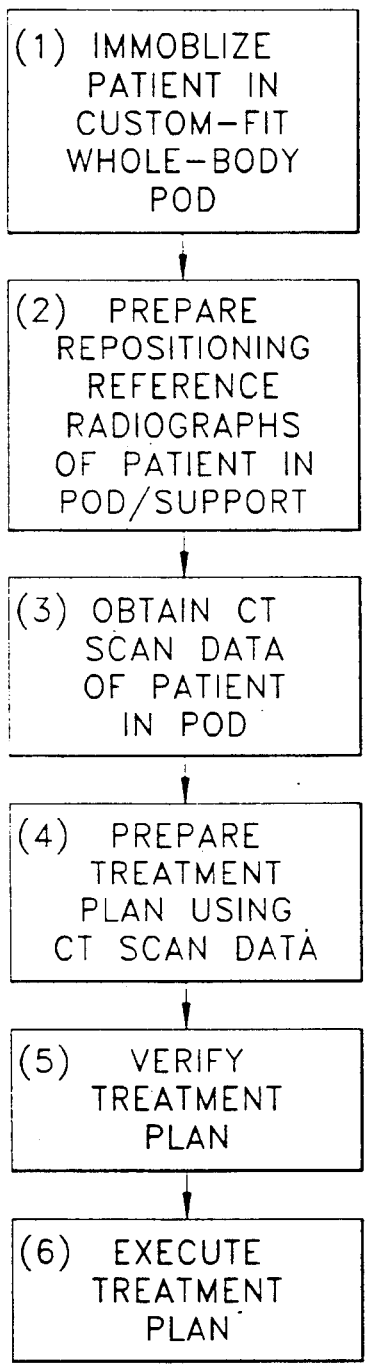
FIG. 4 is a flow chart illustrating the main steps of the alignment method used by the present invention.

Utilizing the above components, the method of alignment of the present invention will next be described. The basic steps of this method are depicted in the simplified flow chart of FIG. 4. Referring to FIG. 4, it is seen that the first step is to immobilize the patient in a custom-fit whole-body pod. The pod, which has been described elsewhere, provides whole-body immobilization for all patients undergoing proton treatment. Once the body is placed inside the pod, the pod supports the patient and immobilizes and positions the patient for all subsequent processes for the treatment.

The second step in the method of alignment as shown in FIG. 4 is to record reference radiographs of the patient within the pod so that on all subsequent treatment days and processes within the treatment, the patient can be repositioned exactly the same within the pod every time. To this end the patient 26 is placed in the custom-fitted pod 24 in a comfortable position. The patient/pod combination is then placed on the simulator table 54 which has mechanical attachments for the pod. Hence, the pod 24 is firmly attached and aligned to the simulator table 54. The table top (or equally the pod structure itself) has embedded wires or other forms of radiographic marks therein that show up on X-ray images. The simulator is aligned with these marks in a reproducible way. The marks then make it possible for the reference radiographs that would subsequently be used to demonstrate the proper patient position to always be taken in the same way. That is, each time the patient returns for treatment, confirmation must be made that the patient is in the pod the same way. The radiographs themselves advantageously provide this confirmation because they are always taken in the same geometry through the use of these embedded markers.

Figure 5:
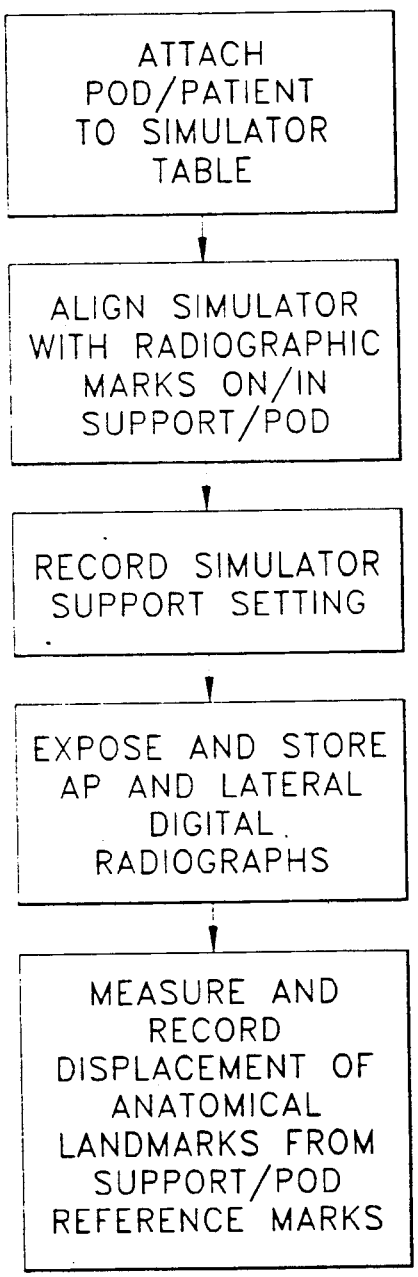
FIG. 5 is a flow chart that further details the second step of the method shown in the flow chart of FIG. 4 wherein repositioning reference radiographs are prepared.
Figure 9:
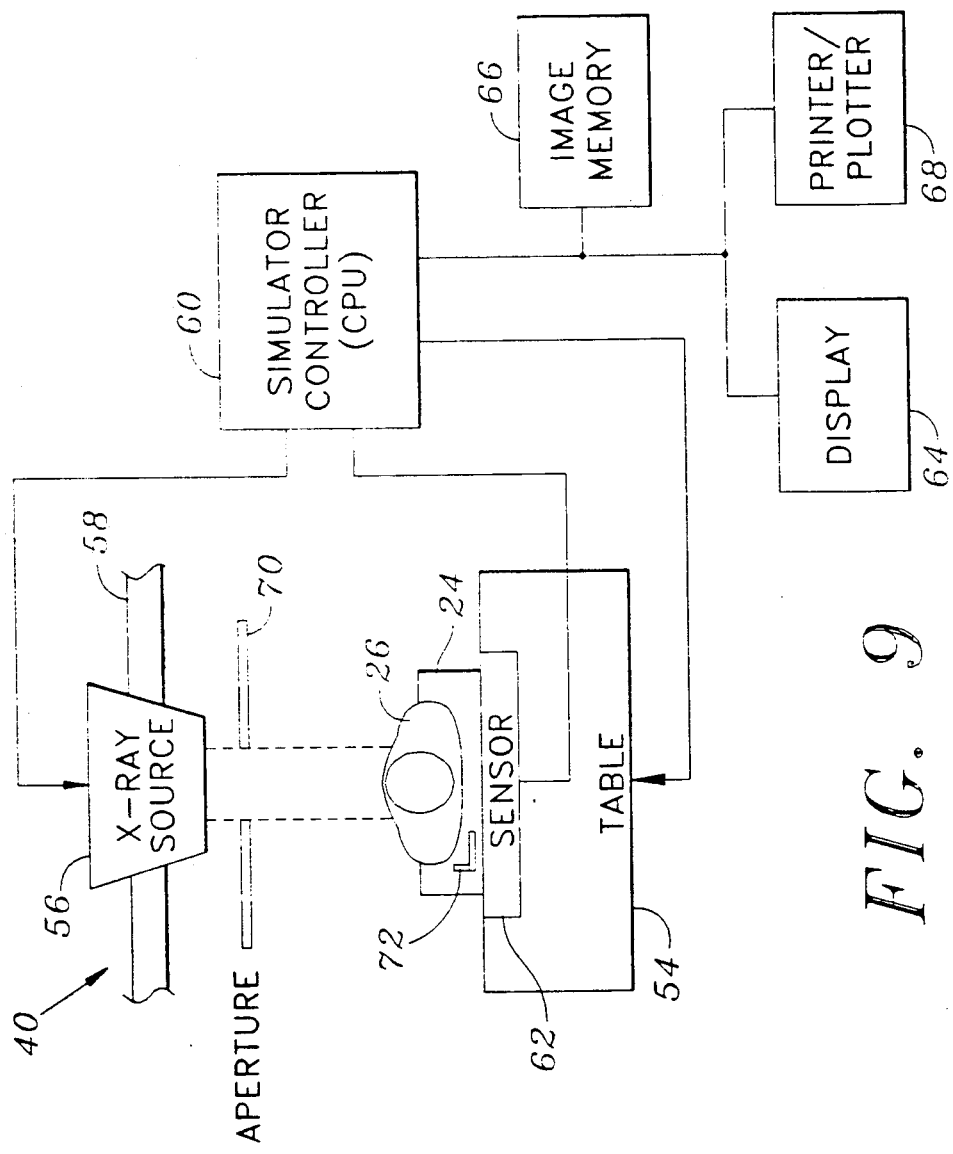
FIG. 9 is a block diagram of the X-ray system of FIG. 1.

To illustrate this second step of the alignment method further, reference is made to FIG. 5, wherein this process of obtaining reference radiographs is further detailed; and to FIG. 9, where a block diagram of the X-ray system 40 is shown in greater detail. The patient 26 in the pod 24 is attached to the simulator table 54. The position of the table 54, as well as the position of the X-ray source 56 on the structure 58, is controlled through the simulator controller 60 using conventional means. A sensor or image receptor 62 is positioned beneath the patient and pod. X-rays received at the sensor 62 are attenuated as a function of the type of matter through which they have passed. Hence, an image is formed at the sensor 62 that can be optically preserved (e.g., on X-ray film) or electronically transferred to the controller 60 as a digital display, i.e., data that defines a matrix of image pixels. This digital display can be displayed on a suitable display device 64, such as a CRT tube, or electronically stored in memory 66. Subsequently, the image can be selectively retrieved for display using the display 64 and/or a printing/plotting device 68. An aperture device 70 provides for further control of the X-ray radiation delivered to the patient.

Using the system shown in FIG. 9, a reproducible geometry for taking lateral and AP radiographs is found by aligning the simulator with reference marks 72 that are embedded in the pod, or embedded in the simulator tabletop. (It is noted that "AP" means anterior/posterior—through from front to back. These radiographs could equally be posterior/anterior, or PA radiographs—from back to front—having the X-ray tube or source 56 underneath the patient and the image receptor, or sensor 62, on top.) AP and lateral radiographs are thus taken in reproducible geometry, and these radiographs become the reference radiographs for all subsequent treatments. As many reference radiographs are taken in reproducible geometry as are deemed necessary in order to provide a sufficient baseline for repositioning the patient within the pod on subsequent treatment days. At least two reference radiographs, one AP and one lateral, are necessary for this purpose. Such radiographs are stored in the image memory 66 and/or hard copies of the radiographs are filed for future reference.

Figure 10A:
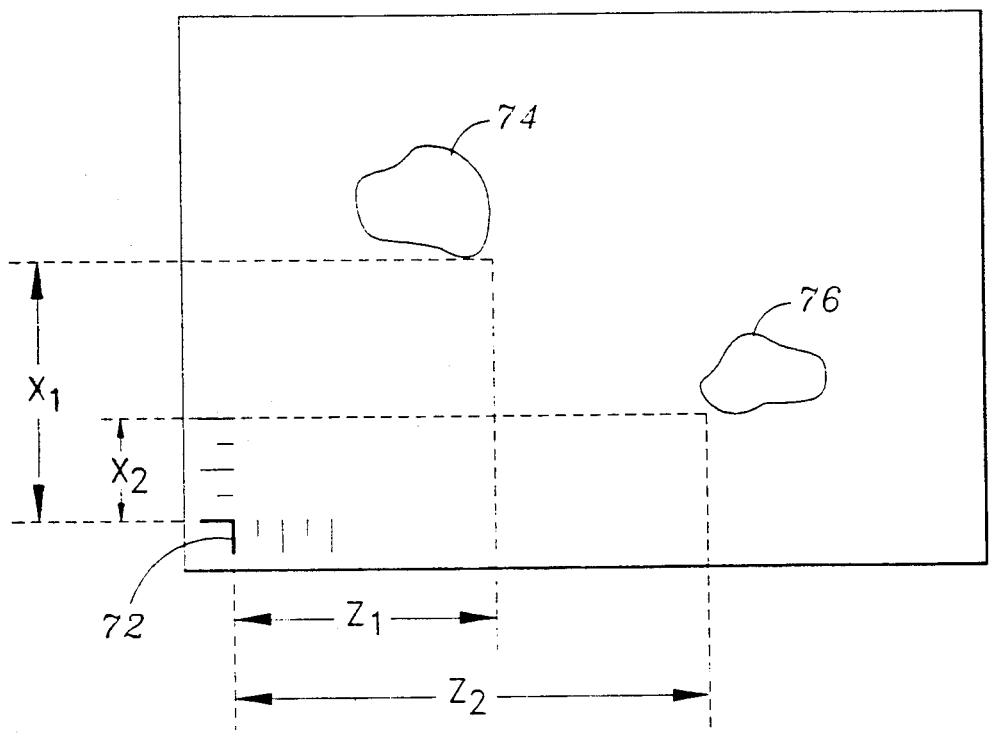
FIG. 10A is a simplified representation of a reference radiograph of the patient in the pod obtained using the X-ray system of FIG. 9.

A simplified representation of a reference AP radiograph obtained using the system of FIG. 9 is illustrated in FIG. 10A. The reference marks 72 appear in the lower left-hand corner. Anatomical landmarks 74 and 76 also appear. Typically, these anatomical landmarks comprise bones or vital organs. The distance to each of these landmarks from the reference mark 72 can be readily measured using either manual or computerized measuring techniques. As shown in FIG. 10A, for example, one corner of the landmark 74 is a distance $x_1$ from the mark 72 in the X direction, and a distance $z_1$ from the mark 72 in the Z direction. These distances are recorded for future reference.

The next step in the alignment method is to obtain CT scan data from the patient while the patient is still in the pod. This step is shown in FIG. 4 as the third step. (It is noted that the second and third steps shown in FIG. 4 could just as easily be reversed.) The CT scan data is used by the present invention to generate a facsimile of a radiograph—a sort of "synthetic radiograph"—referred to hereafter as a digitally reconstructed radiograph, or DRR. The generation of a DRR is possible because a CT scan has all the tissue densities in very fine detail. These tissue densities are readily digitized, thereby providing a map of the tissue densities, in three dimensional form, with each point of the three dimensional map comprising a digital number that identifies a relative value of the tissue density at that point. It thus becomes a relatively straightforward task, especially for a computer, to numerically pass rays through the mapped tissue data from some presumed source location to some presumed image plane and generate or compile a synthetic view or image, i.e., the DRR, of what a radiograph should look like if an X-ray, or equivalent image-forming beam, were passed through the tissue along this same path. The path along which the X-ray passes, as well as the path that is numerically passed through the mapped tissue data, may be thought of as a "view line". Such a view line is normal to the plane of the image, whether the image comprises a "real" radiograph image or a synthetic digitally reconstructed image.

Figures 6A, 6B:
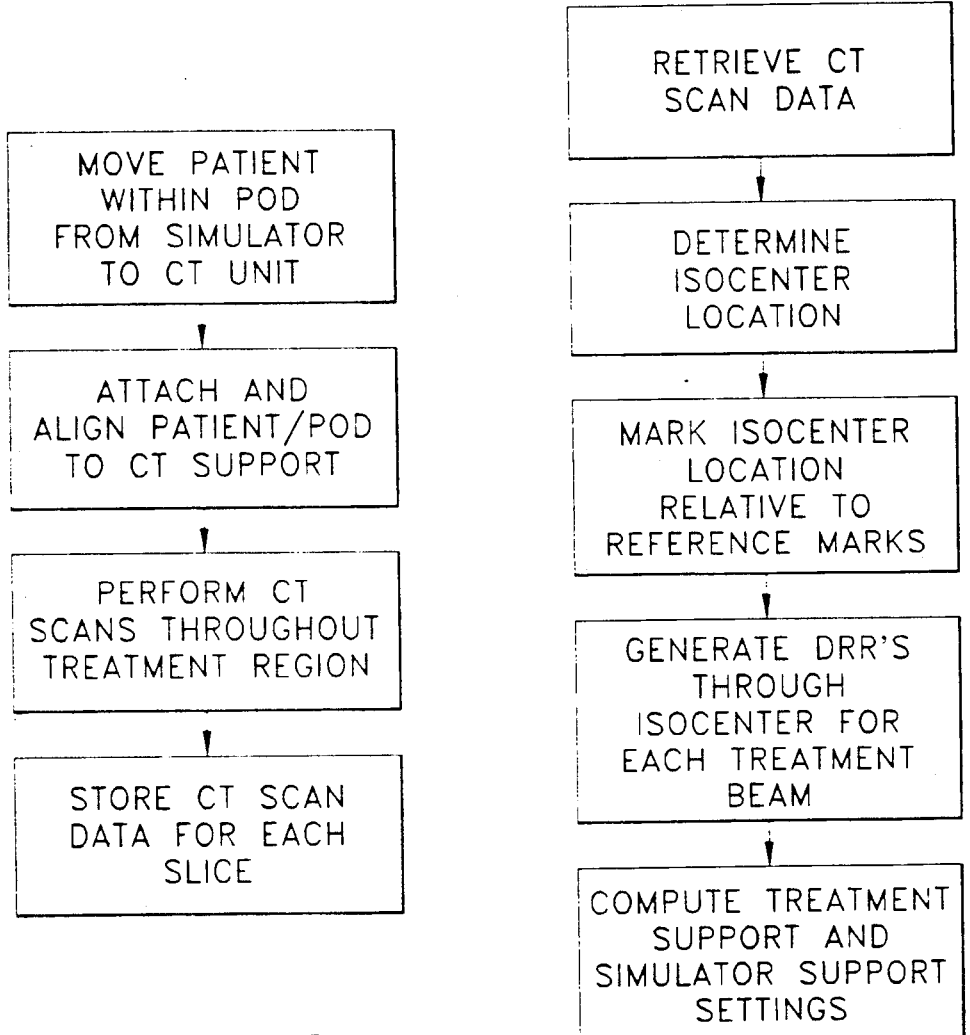
FIG. 6A is a flow chart further expanding the third step of the method shown in the flow chart of FIG. 4 wherein CT scan data is obtained from the patient while positioned in the patient pod.
FIG. 6B is likewise a flow chart that sets forth some of the details of the fourth step of the method shown in the flow chart of FIG. 4 wherein the "treatment plan" is prepared.

In accordance with this third (or second) step of obtaining the CT scan data, which is further detailed in the flow chart of FIG. 6A, the patient is transported to the CT scan device 44 (FIG. 1) without moving the patient within the pod, and while having the patient lie still. The pod is attached mechanically to a table top of the CT unit. The CT table top or the pod itself also contain radiographic markers which are visible on the CT image. A sequence of CT images are then taken which cover the entire region on the body that is intended for proton treatment. These images are commonly referred to as "slices" because they present a dramatic visual representation of a particular cross section of the patient, almost as though a "slice" of tissue had been removed from the patient.

Figure 11:
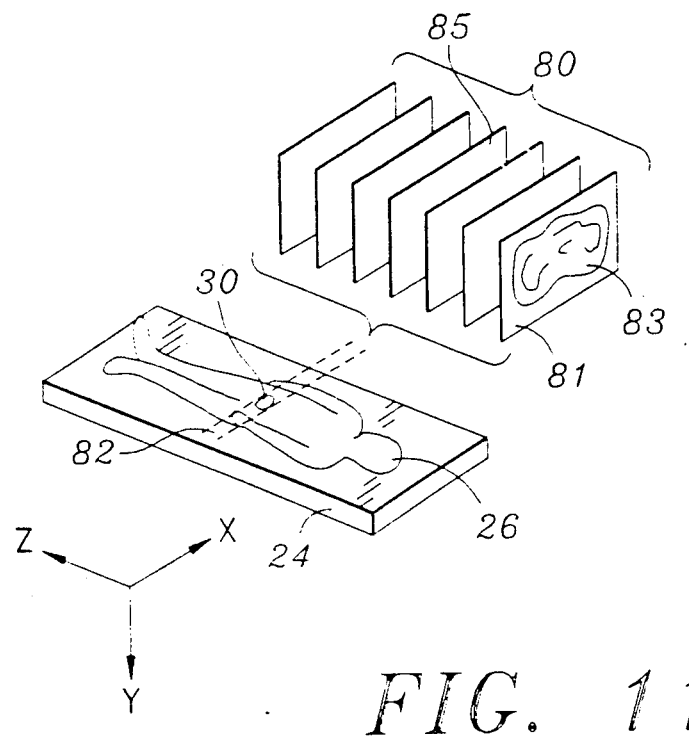
FIG. 11 illustrates the concept of taking cross-sectional "slices" in the patient using the CT scan system of FIG. 1.

This concept of obtaining CT slices is further illustrated in FIG. 11 wherein a series of CT images 80 are taken across a width 82 of the midsection of the patient 26 surrounding the selected target volume 30. (Obviously, the CT slices can be taken of any desired region of the patient. The transverse orientation of the midsection slices shown in FIG. 11 is only exemplary.) Each of the slices, such as a first slice 81, provides a detailed two-dimensional image 83 of the cross section of the patient at the particular location where the slice is taken. As has been indicated, these two dimensional images are digitized for easy storage and retrieval. Further, the combined image data of all of the adjacent slices provides a detailed three dimensional representation, or digital map, of the particular volume of the patient scanned by the CT system. This detailed, three dimensional, digitized image of the region surrounding the target volume 30 plays an important role in formulating the treatment plan, as explained below. The manner of obtaining CT scan data, as well as the manner in which such data are stored, retrieved and displayed are well documented in the art and will not be repeated herein.

It is noted that part of the process of obtaining the CT scan data is aligning the slice indicator of the CT unit 44 with a mark on the pod which represents the zero bed position. This sets what is referred to as the Z-axis reference or origin. In this case, similar to the coordinate systems shown in FIGS. 1 and 2, the Z-axis is along the long axis or longitudinal axis of the patient. Once the CT scan data has been obtained and stored, the patient is typically allowed to get out of the pod. Normally, at this time the patient would return home and come back a few days later, after their treatment plan has been developed.

The next step of the alignment method or process of the present invention is to prepare a suitable treatment plan. This is identified as step four in FIG. 4. This treatment plan is prepared using the patient's CT scan data as a representation of the patient, which representation includes the target volume 30 that is to be treated. A key part of preparing such a treatment plan is using a computer simulation of the proton beam directed to the target volume 30. Through such simulation, appropriate beam angles and beam energies can be determined to best irradiate the target volume. Typically, the beam angles are measured relative to known reference points marked on the CT slices, e.g., the target volume itself. The beam energies are set appropriately to control the penetration depth of the beam. Once a proposed beam angle and energy are selected, a simulation of the irradiation process may be carried out and displayed on a suitable display screen of the computer. Alternatively, or conjunctively, printouts of the results of the simulated irradiation may be prepared, for the treatment-planning physician and/or treatment-planning physicist to examine. Through this computer simulation process, which typically involves several iterations, an optimum treatment plan can be formulated that defines the number of beams that should be used to treat the target volume, including their respective energy levels and entry angles. Once the plan is formulated, the various settings required for the simulator system 22 and beam delivery system 20, needed to produce the specified beam angles and energies, can be calculated.

Figure 12:
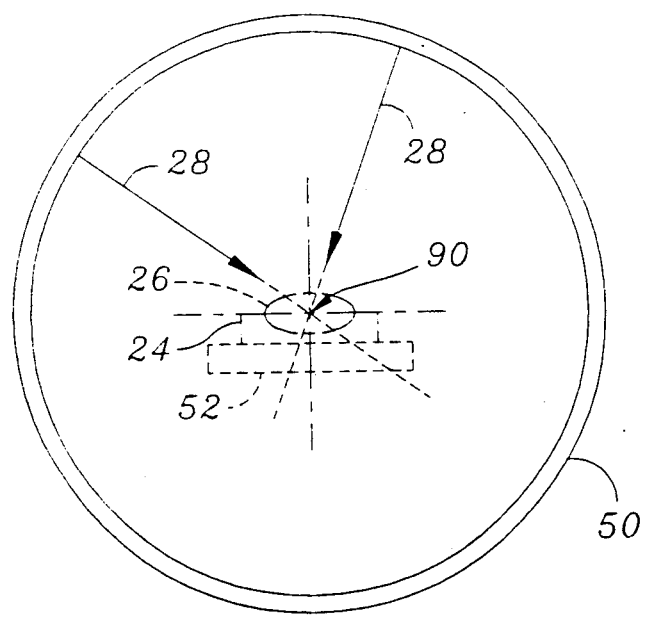
FIG. 12 illustrates the isocenter of the beam delivery system, and illustrates the concept of positioning the patient within the beam delivery system so that the isocenter coincides with a desired target volume.

A primary component of formulating the treatment plan is to determine the location of the treatment center isocenter within the body tissue. The treatment center isocenter is a physical point in space at which the beams from the beam delivery system converge, regardless of the angle from which the beams emanate. In other words, with reference to FIG. 12, for a beam delivery system 20 of the type having a gantry 50, the isocenter is that point 90 in the center of the gantry at which the beams 28 converge regardless of the position around the circumference of the gantry 50 from which the beams originate. It is thus the purpose of the treatment plan to bring the tissue volume of interest, e.g., the target volume 30, to a particular point in space having a fixed geometrical relationship relative to the isocenter 90. Typically, for many treatment plans, the target volume 30 will be brought directly to the isocenter 90 of the beam delivery system, as seen in FIG. 12 where the patient 26 (shown in dotted lines) is positioned relative to the isocenter 90 so that the isocenter 90 lies within the treatment volume 30. For other treatment plans, however, it may be desirable to place the target volume at some specified distance away from the isocenter. This is because the beam is diverging somewhat as it travels away from its source. Hence, for example, if a larger beam were desired, then the patient may be positioned so that the isocenter is outside of the target volume 30, and perhaps even outside of the patient, thereby taking advantage of the divergence of the beam to get a larger physical field size. For purposes of the present invention, therefore, the treatment plan specifies the position the target volume 30 is to assume relative to the isocenter 90. Once this position is known, the patient may be moved by simply moving the patient table 52, e.g., by lowering, raising, rotating, and/or laterally or longitudinally moving the table to a calculated location that will position the target volume 30 at the specified position relative to the isocenter 90.

Figure 13:
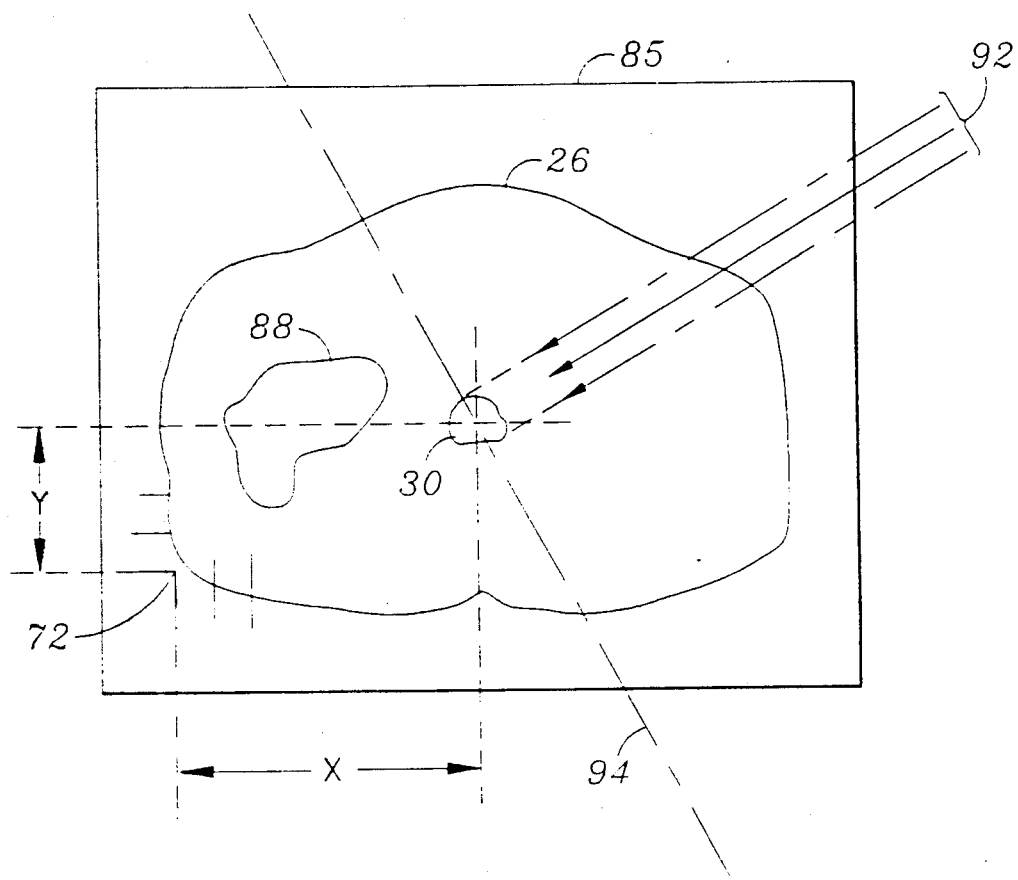
FIG. 13 shows a representative CT slice obtained using the CT scan system of FIG. 1, and illustrates some of the considerations involved in formulating an appropriate treatment plan, such as marking the isocenter on the CT slice to coincide with the approximate center of the target tissue, and selecting a beam to irradiate the target tissue at a desired angle.

The tissue location at which the isocenter is to be located is determined in accordance with the present invention by identifying a central CT slice that passes through the tumor or target volume 30. That is, the CT slice that most closely passes through the center of the target volume, is identified. For example, with reference to FIG. 11, such a central CT slice might be the slice 85. Once this central CT slice is identified, this determines the Z coordinate of the tissue isocenter. (The tissue isocenter is that point which is to be aligned with, or to have a fixed geometrical relationship with, the beam delivery isocenter 90.) The transverse image, that is image shown on the slice 85, is then examined for the purpose of defining the X-Y coordinates of the tissue isocenter. Normally, this will be near the center of the target volume 30. To illustrate, a simplified representation of the central CT slice 85 may appear on a computer display screen as shown in FIG. 13. The target volume 30 is shown as being positioned near the center of this slice, and an anatomical landmark 88 is also shown to the left of the target volume. The desired tissue isocenter is chosen, for purposes of this example, to be approximately in the center of the target volume 30. Hence, the tissue isocenter has coordinates X and Y, as measured from the reference mark 72 as shown.

Figure 14:
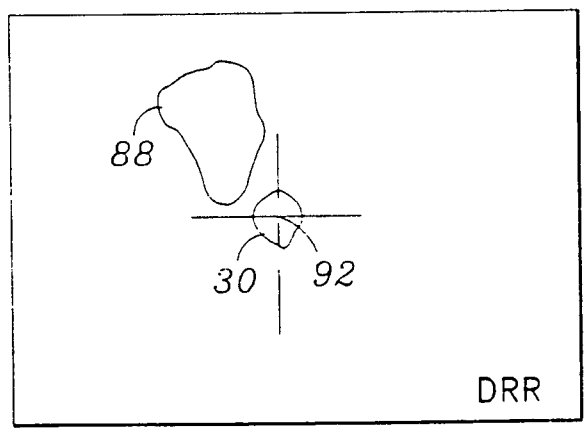
FIG. 14 depicts a simplified digitally reconstructed radiogram (DRR) obtained from the CT slice (and adjoining slices) of FIG. 13.

Once the X-Y coordinates of the desired tissue isocenter have been selected, this tissue isocenter position is marked in an appropriate way so that it can be "seen" as the CT scan data is subsequently analyzed. Marking may be accomplished simply by placing a graphic mark at the selected tissue isocenter location as the transverse image is displayed on a computer screen, using a "mouse" or equivalent computer graphics tool. Advantageously, because the CT scan data is digitized, this mark will appear in all digital views of the patient. Hence, one significant advantage provided by utilizing the three dimensional digitized CT scan data in formulating a treatment plan is that a beam's eye view (BEV) may be presented to the treatment planning physician or physicist of the target volume. This beam's eye view is simply a view of the target volume as seen through the CT image in the direction of the beam, as if the eye were the source of the beam. A representative BEV of a beam 92, as shown in FIG. 13, is depicted in FIG. 14.

The mark of the tissue isocenter appears in the beam's eye view, as well as a cross-mark that represents the center of the beam. The isocenter of the beam system, of course, is always somewhere along that cross-mark. Therefore, in computer simulation, the patient's table is adjusted, up or down, left or right, in or out, until the cross-mark representing the central axis of the beam is right on the mark indicating the tissue isocenter location made on the transverse image of the central CT slice. Once this adjustment has been made, the isocenter of the system is aligned with the tissue isocenter and the treatment beam will pass through the tissue isocenter. If the tissue isocenter is to be common to several different treatment beams, which is by far the simplest way to treat a patient, then the same tissue isocenter mark is retained and simulated treatment beams from different directions are aligned to pass through the same mark. This alignment is achieved, whether in computer simulation or actual treatment, by simply rotating the gantry.

As part of the treatment planning process, digitally reconstructed radiographs (DRR's) are generated for the beam's eye view centered on the isocenter with the gantry angle presumed to be the treatment gantry angle. As indicated above, a simplified representation of a beam's eye view DRR is shown in FIG. 14. This DRR of FIG. 14 represents a BEV of the beam 92 of FIG. 13, and the image shown in the DRR of FIG. 14 lies in the image plane represented by the line 94 in FIG. 13. Additional DRR's are produced from the CT scan data of the AP and lateral projections of the X-ray or other image-producing beams. These DRR's are used as reference radiographs throughout the treatment of the patient to make sure that the patient has been returned to the proper location for the treatment plan being used for that patient. Each DRR is projected on a view line through the tissue isocenter. The AP and lateral projections were initially projected (prior to determining the tissue isocenter) as orthogonal pairs at relatively arbitrary points for the purpose of determining if the patient has been returned to the pod correctly. Once the tissue isocenter has been defined, however, an orthogonal pair of DRR's that projects through the isocenter for each treatment beam is preferred. This is because what is seen in an AP and lateral projection represents the way the anatomy appears in the simplest projection or simplest representation for interpretation. Oblique radiographs through the patient are sometimes very difficult to understand because all the anatomy has been rotated and it doesn't look as it normally is depicted. An orthogonal pair, on the other hand, offers the advantage of the presenting the anatomy in the usual directions. Further, such directions can be readily translated directly into the orthogonal motions of the patient table support system. For example, if a lateral beam is coming through the patient and the anatomy is displaced too far up, then one knows to simply drop the table down. Hence, a one-to-one correspondence is maintained between what must be done to align the patient and the way the anatomy is presented. In contrast, if the beam enters at an oblique angle, a misalignment may still be evident, but it is not always immediately apparent what must be done to the patient table to correct the misalignment. Hence, it is very helpful to have both AP and lateral DRR's that are projected through the tissue isocenter to facilitate the repositioning process. However, it is also preferrable to have a beam's eye view projection through the tissue isocenter to provide an indication of how the actual beam is projected through the tissue.

At this point, it may be helpful to make a distinction between simulator (e.g., X-ray) geometry and treatment geometry. These geometries may be different for different setups. The treatment geometry may be considered as the distance from the source of protons to the isocenter of the treatment machine. This treatment distance is not necessarily the same as the simulator geometry, or the distance from the source of X-rays (or other image-producing rays) to the isocenter of the simulator. The simulator distance, for example, is typically closer than the treatment distance. This is because the proton gantry is inherently large and cannot fit in a normal room. The simulator, on the other hand, almost always fits within a normal room. In fact, one of the advantages of using a simulator as disclosed herein is that it is relatively small and does fit within a normal room. This is significant because much of the time and effort involved in the alignment method occurs using only the simulator, without tying up the large and cubersome treatment system. Hence, in the descriptions presented herein, reference may be made to "simulator geometry," which is how far the source may be placed away from the tissue isocenter of the simulator system, and "treatment geometry," which is normally a much larger distance, roughly equivalent to the distance between the proton source and the axis of rotation of the gantry. Because of this difference between the simulator and treatment geometries, it must be recognized that one cannot duplicate exactly with X-rays on the simulator system precisely what will occur with proton beams using the beam delivery system for treatment of the patient. Again, this is because the respective divergence characteristics of the two beams do not quite match.

During the treatment-planning process, as has been indicated above, a number of DRR's (digitally reconstructed radiographs), or synthetic radiographs as they are sometimes called, are generated. Typically, once the tissue isocenter is located, the AP and lateral DRR's through the isocenter are always made in simulator geometry. Further, the X-ray tube 38 (FIG. 1) included in the nozzle of the beam delivery system is typically placed in simulator geometry. The beam's eye view DRR's, on the other hand, are produced in both simulator and treatment geometry. Using these two different geometries, allows various sets of DRR's to be generated from the patient CT scan data that isolates the manner in which the patient should be positioned for all treatments, both simulated and actual.

With the XYZ coordinates of the tissue isocenter identified, sufficient information exists to accurately reposition the patient in the simulator system 22 or the beam delivery system 20 so that the tissue isocenter can be aligned with the system isocenter for subsequent simulation or treatment processes. Further, knowing the location of the isocenter, the settings for both the treatment support (table) system and the simulator support system, as well as both the gantry or X-ray entry angle systems, can be computed. It is these settings, along with the tissue isocenter locations, that comprise the "output" of the treatment planning step of the alignment method described herein. Such settings are generated for each beam that is to be used to irradiate the target volume.

Figure 7:
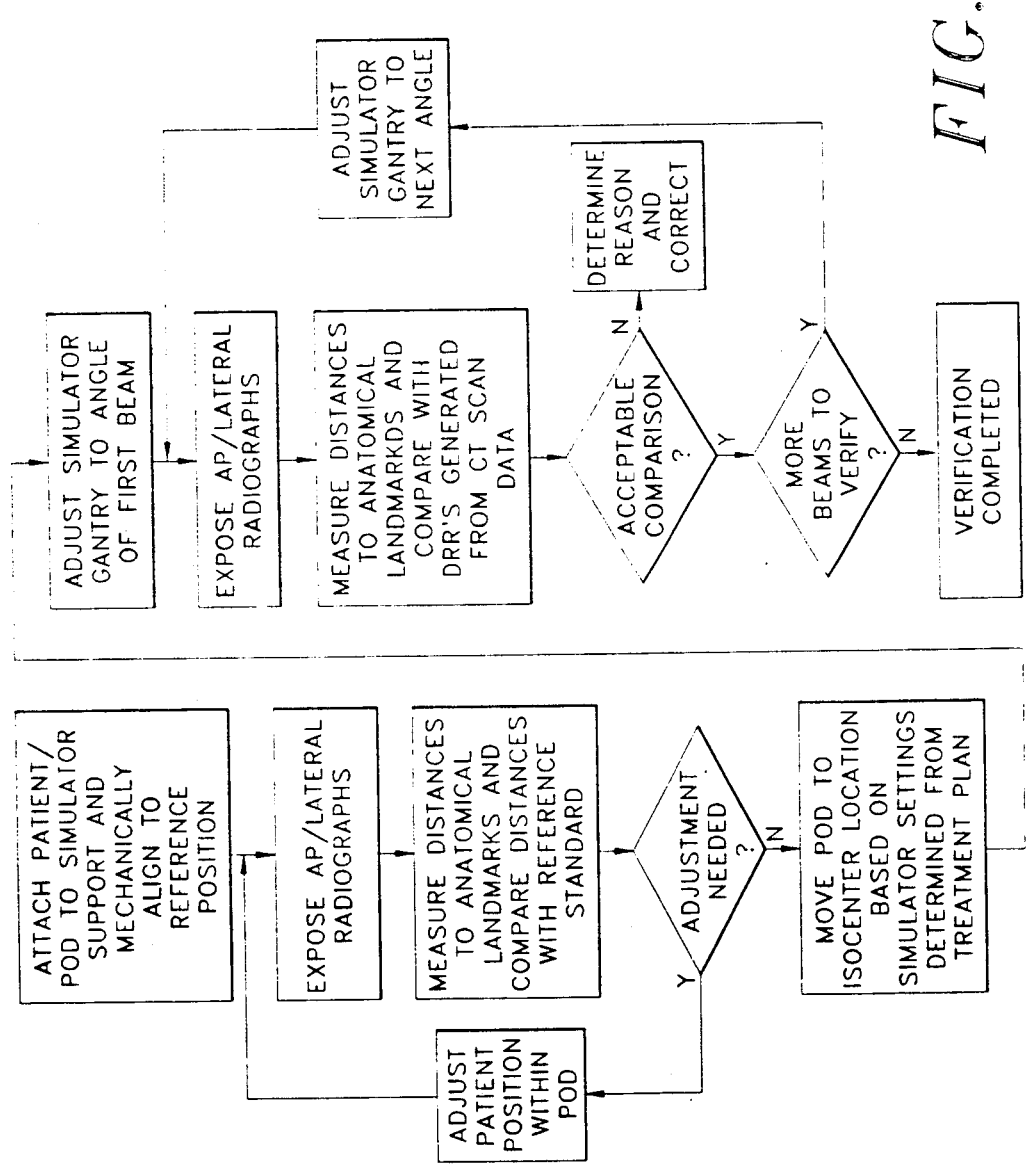
FIG. 7 is also flow chart that further expands the fifth step of the method shown in the flow chart of FIG. 4 wherein the treatment plan is verified.
Figure 10B:
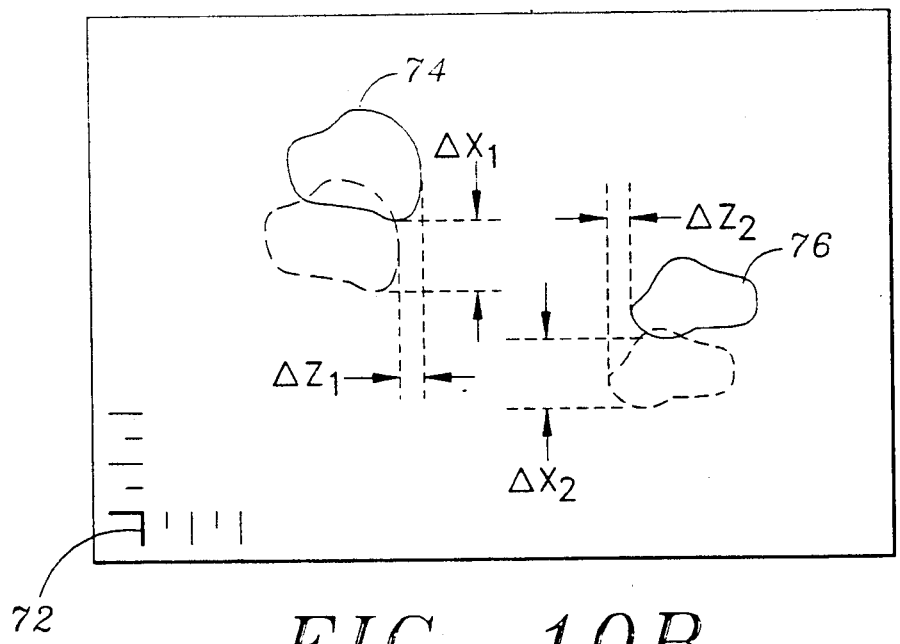
FIG. 10B is a simplified representation of a radiograph as in FIG. 10A obtained after the patient has been repositioned within the pod, and compares the difference between the reference radiograph of FIG. 10A and that of FIG. 10B.

Once the treatment plan is finalized, and the tissue isocenters for each beam have been specified, and the corresponding simulator and treatment table and angle settings have been determined, the patient returns to the medical center for physical treatment simulation. This physical treatment simulation is identified in FIG. 4 as step 5. "Verify Treatment Plan." A more detailed flow chart of this physical treatment simulation process is shown in FIG. 7. The patient comes to the simulator system 22, and is positioned within the pod 24 in the same way as he or she was positioned for the CT scan and treatment planning. The pod, with the patient in it, is then attached to the table support 54 (FIG. 9). Lateral and AP radiographs are then repeated, using exactly the same geometry as was used on the day the CT scan data was obtained. If necessary, the patient's position within the pod is adjusted slightly, e.g., by pulling on the sheet or asking the patient to move a bit, until the AP and lateral radiographs have exactly the same relationship between anatomical marks within the image to an origin that's also superimposed on the image as were present on the day of the CT scan. This process is illustrated in FIG. 10B. In FIG. 10B, the anatomical landmarks 74 and 76 that were measured on the day of the CT scan are shown with dashed lines. Recall from FIG. 10A that these landmarks were measured as being a distance $x_1$, $z_1$ and $x_2$, $z_2$ from the reference origin 72. In FIG. 10B, these landmarks are not positioned precisely the same relative to the origin 72 as they were previously. The difference in position is represented in FIG. 10B as delta $x_1$ and delta $z_1$ for landmark 74, and delta $x_2$ and delta $z_2$ for landmark 76, this difference being determined by measuring the distance to the reference origin 72. Note that the reference origin 72 will always be in the same position because it is mechanically embedded in either the pod 24 or the table 26. Hence, the difference indicated in FIG. 10B can only be attributed to a slight difference in the position of the patient within the pod. Thus, the patient would be moved slightly in order to reduce this difference to a negligible amount.

Once it has been demonstrated that the patient is positioned in the pod precisely as he or she was for the treatment planning CT scan, the simulator table is moved to place the tissue isocenter location at the simulator isocenter location according to the position settings determined by the treatment planning process. Once so positioned, additional anterior/posterior and lateral PSR radiographs may be taken through the simulator isocenter. The gantry of the simulator (i.e., the X-ray source 56 coupled to the structure 58—FIG. 3) is then turned to the angulation of the specified treatment beam, and a beam's eye view PSR in simulator geometry is taken. This beam's eye view advantageously allows the physicaian to see the tissue that will be irradiated with the protons. Hence, by comparing this beam's eye view PSR with the corresponding beam's eye view DRR, formulated in the treatment planning process, a decision can be made as to whether the target volume will be irradiated as desired. If an acceptable comparison is made, that is, if the two views present substantially the same image, then the physical simulation has been successfully completed. If the two views are not substantially the same, then that is an indication that something is not right. For example, the table position may have not been properly set, or the agulation angle may not be correct. If an irreconcilable discrepancy exists, which shouldn't happen unless the patient has lost (or gained) weight or some mistake has been made, then the whole process, including gathering new CT scan data and formulating a new treatment plan, will likely have to be repeated.

As seen in the flow chart of FIG. 7, the physical simulation process is repeated for each beam specified in the treatment plan.

The comparison of the various views or images that are frequently made throughout the alignment method are preferably made by comparing the locations of anatomical landmarks appearing within the images to previously recorded locations corresponding to the same landmarks in the same views. Advantageously, commerically available software programs, typically graphic-oriented software programs, exist that facilitate such comparisons. Using such programs, the various images can be displayed on a computer screen and referenced to the designated reference origin, e.g., the mark 72. A cursor is then moved to the landmark whose position is to be measured, a switch is toggled, and the measurement is automatically made and recorded. Simple programming, readily accomplished by those skilled in the art, may also be employed to automatically compare the measured distances with previously stored values so as to automatically indicate whether an acceptable comparison has been made.

Figure 8:
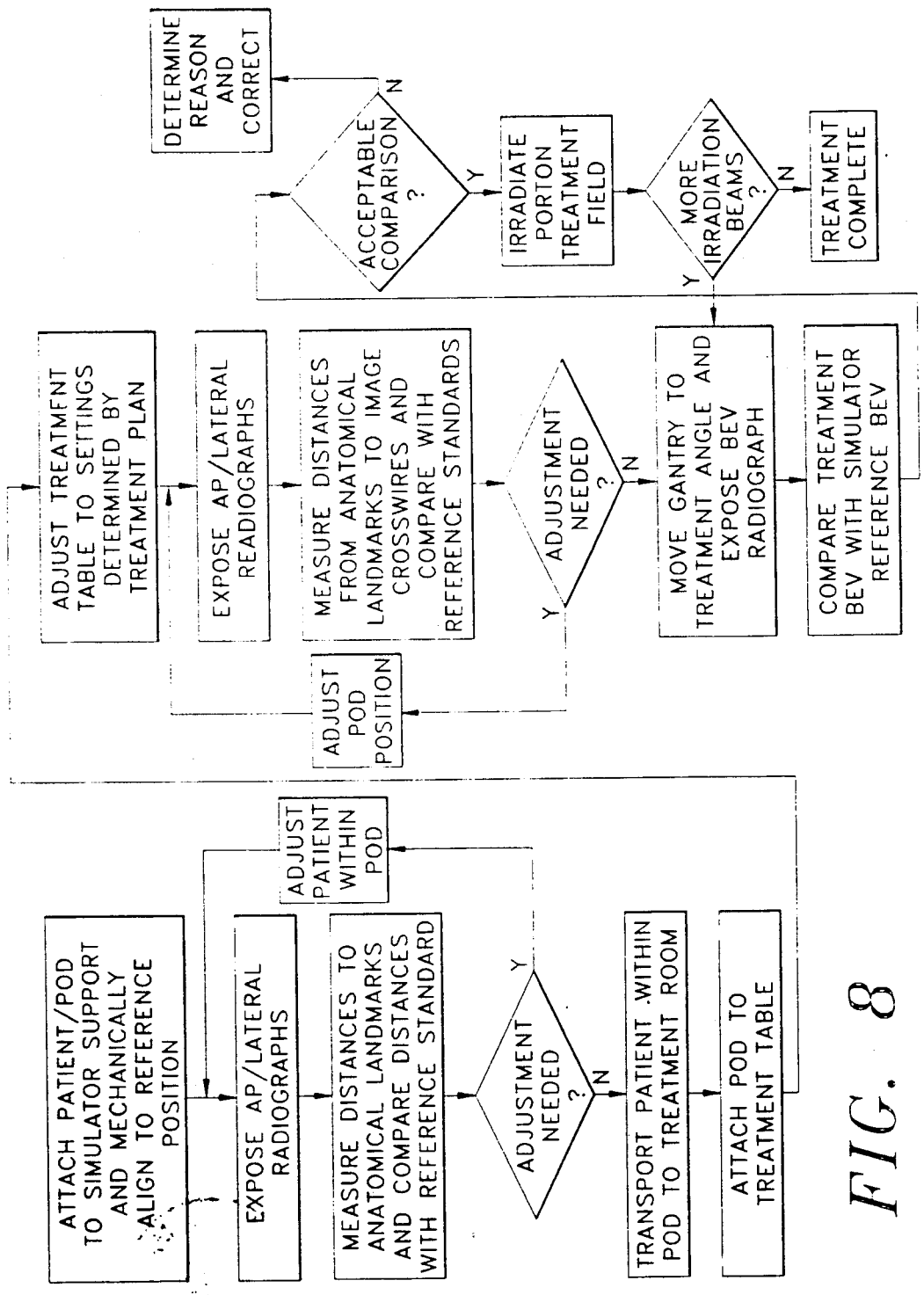
FIG. 8 is a flow chart further detailing the sixth step of the method shown in the flow chart of FIG. 4 wherein the treatment plan is executed.

Once the physical simulation, or verification of the treatment plan has been completed, the patient and pod are transported to the treatment room and the treatment plan is executed. This is represented as step 6 in the flow chart of FIG. 4. This step of executing the treatment plan is further detailed in the flow chart of FIG. 8.

The first part of the treatment execution method corresponds to the first part of the physical simulation and is concerned with making sure the patient is properly positioned within the pod before any treatment is provided. That is, on each treatment day, the patient first comes to the simulator, climbs into the pod, is radiographed with AP and lateral views, and is repositioned within the pod until these reference images are exactly the same as for the day the CT scan was taken. Then, once having demonstrated that he or she is in the pod correctly, the patient is transported to the treatment room. Once in the treatment room additional radiographs are taken through the treatment isocenter, using strategically placed X-ray sources, to confirm that the patient is in proper treatment position. As has been indicated, one of the X-ray sources is the X-ray source 38 (FIG. 1) positioned in line with the proton beam. This X-ray source duplicates the geometry of the simulator. The radiographs thus taken—AP, lateral, and beam's eye view—are compared as required with the PSR simulation radiographs, as well as with the DRR radiographs, to confirm that the patient is in the correct treatment position. Once this final confirmation is obtained, the target volume is irradiated with the proton beam (or other charged particle beam) in accordance with the treatment plan.

While the invention described herein has been described with reference to a particular embodiment and application thereof, numerous variations and modifications could be made thereto by those skilled in the art without departing from the spirit and scope of the invention as claimed. Accordingly, the true scope of the invention should be determined with reference to the claims set forth below.

What is claimed is:

1. A method for irradiating a volume of tissue within a patient with a charged-particle beam, said method comprising the steps of:
   (a) immobilizing the patient;

(b) obtaining CT scan data of a region of tissue within said immobilized patient that includes said volume of tissue;

(c) preparing a treatment plan using said CT scan data by identifying an isocenter point having a fixed geometrical relationship relative to said volume of tissue at which said charged-particle beam is to be directed, determining an entry angle for said charged-particle beam, and generating an image reconstructed from said CT scan data that identifies how the volume of tissue should appear when viewed along said entry angle through said isocenter point;

(d) verifying said treatment plan by performing a physical simulation of the irradiation of said volume of tissue by said charged particle beam, said physical simulation including, (1) directing an image-forming beam along said entry angle at said isocenter point, said image-forming beam producing an image of the tissue through which it passes, and (2) comparing the image formed by said image-forming beam with said reconstructed image from said CT scan data along said entry angle verify that the charged particle beam will properly irradiate said volume of tissue;

(e) executing said treatment plan by directing said charged-particle beam at said isocenter point.

2. The method of claim 1 wherein the step of immobilizing the patient comprises immobilizing the patient relative to a holding device, and wherein the method further includes preparing repositioning reference radiographs of the patient and the holding device before releasing the patient from the holding device, said repositioning reference radiographs providing reference information that identifies the position of the immobilized patient relative to the holding device.

3. The method of claim 2 further including the steps of:

releasing the patient from the holding device after said CT scan data has been obtained; and repositioning said patient within said holding device prior to verifying said treatment plan, said repositioning being performed by using said reference information to verify that the patient is positioned relative to said holding device in the same manner as the patient was originally positioned relative to said holding device.

4. The method of claim 1 wherein the step of preparing said treatment plan includes:

identifying a tissue isocenter within said volume of tissue defined by said CT scan data that is to be irradiated with said charged-particle beam;

marking said identified tissue isocenter; and reconstructing orthogonal reference radiographs from the CT scan data that pass through said marked tissue isocenter.

5. The method of claim 4, wherein the step of preparing said treatment plan further includes performing a computer simulation of irradiation with said charged-particle beam.

6. The method of claim 5 wherein said computer simulation is performed by directing a simulated charged-particle beam at said isocenter point through said marked tissue isocenter of said CT scan data.

7. The method of claim 4 wherein said physical simulation further includes:

positioning the immobilized patient to receive said image-forming beam;

comparing the image formed by said image-forming beam with at least one of the reconstructed orthogonal radiographs; and adjusting the position of the immobilized patient relative to the image-forming beam as required in order to align the image focused by said image-forming beam with said at least one of the reconstructed orthogonal radiographs.

8. The method of claim 7 wherein the step of executing said treatment plan includes delivering said charged-particle beam to the volume of tissue within said patient only when the position of the patient relative to the charged-particle beam is adjusted so that the charged-particle beam enters the patient with the same alignment as said image-forming beam.

9. A method for aligning a charged-particle beam with a volume of tissue, such as a tumor, of a patient undergoing radiation therapy, said method comprising the steps of:

immobilizing the patient;

digitally mapping tissue densities of the patient in a region surrounding said volume of tissue;

within data defining said digitally mapped tissue densities identifying and marking a portion of the data that defines the volume of tissue to be irradiated by said charged-particle beam;

reconstructing at least one image of the tissue densities from said digitally mapped tissue densities, said at least one reconstructed image having a view line normal thereto that passes through said marked data;

forming a radiographic image of the tissue of said patient taken along said view line;

quantitatively comparing said radiographic image to said reconstructed image;

adjusting the position of the immobilized patient relative to the radiographic image until any difference between said radiographic image and said reconstructed image is minimized; and aligning the charged-particle beam to be delivered to said volume of tissue with the view line of said radiographic image after the step of adjusting has been completed.

10. The alignment method of claim 9 wherein the step of reconstructing at least one image of the tissue densities comprises reconstructing at least two orthogonal images from the digitally mapped tissue densities.

11. The alignment method of claim 9 wherein the step of quantitatively comparing said radiographic image to said reconstructed image comprises comparing distances between anatomical landmarks appearing in both images to a common reference point.

12. The alignment method of claim 9 wherein the step of immobilizing the patient comprises immobilizing the patient relative to a holding device, and wherein the method further includes preparing repositioning reference radiographs of the patient and the holding device before releasing the patient from the holding device, said repositioning reference radiographing providing reference information that identifies the position of the immobilized patient relative to the holding device.

13. The method of claim 12 further including the steps of:

removing the patient from the holding device once the digitally mapped tissue densities has been obtained; and repositioning the patient in said holding device prior to forming the radiographic image of the patient along said view line.

14. A system for aligning a charged-particle beam with a volume of tissue in a patient undergoing radiation therapy, said system comprising:

means for immobilizing the patient;

means for digitally mapping tissue densities of the patient in a region surrounding said volume of tissue, said digitally mapping means providing digitally mapped tissue density data that defines the tissue surrounding and including said volume of tissue;

means for identifying and marking data within said digitally mapped tissue density data that defines the volume of tissue that is to be irradiated by a charged-particle beam;

means for reconstructing at least one image of the tissue densities from said digitally mapped tissue density data, said at least one reconstructed image having a view line normal thereto that passes through said marked data;

means for forming a radiographic image of the tissue of said patient taken along said view line;

means for quantitatively comparing said radiographic image to said reconstructed image;

means for adjusting the immobilized patient until any position difference between said radiographic image and said reconstructed image are minimized; and means for aligning the charged-particle beam to be delivered to said volume of tissue with the view line of said radiographic image after the differences between the radiographic and reconstructed images have been minimized.

15. The alignment system of claim 14 wherein said means for reconstructing at least one image comprises means for reconstructing two orthogonal images.

16. The alignment system of claim 15 wherein said orthogonal images comprise AP (Anterior Posterior) and lateral images.

17. The alignment system of claim 16 wherein said means for reconstructing at least one image includes means for reconstructing a beam's eye view image, said beam's eye view image comprising an image depicting the tissue densities as would be seen by an eye placed at the source of the image forming beam.

* * * * *

Disclaimer 5,117,829—Daniel W. Miller, Yucaipa; James M. Slater, Redlands, both of Calif. PATIENT ALIGNMENT SYSTEM AND PROCEDURE FOR RADIATION TREATMENT. Patent dated June 2, 1992. Disclaimer filed April 17, 1997, by the assignee, Loma Linda University Medical Center.

Hereby enters this disclaimer to claims 1, 4-11 and 14-17 of said patent.
*(Official Gazette,* June 17, 1997)